United States Patent [19]

Burek et al.

[11] Patent Number: 5,256,138
[45] Date of Patent: Oct. 26, 1993

[54] ELECTROSURGICAL HANDPIECE INCORPORATING BLADE AND CONDUCTIVE GAS FUNCTIONALITY

[75] Inventors: Paul P. Burek, Aurora, Colo.; William J. Bowers, Irvine, Calif.

[73] Assignee: The Birtcher Corporation, Irvine, Calif.

[21] Appl. No.: 592,810

[22] Filed: Oct. 4, 1990

[51] Int. Cl.⁵ ............................................. A61B 17/39
[52] U.S. Cl. ....................................... 606/42; 606/45; 606/49
[58] Field of Search ................. 606/34, 40, 41, 42, 606/45, 49; 219/121.5, 121.51, 121.52

[56] References Cited

U.S. PATENT DOCUMENTS

| | | |
|---|---|---|
| 2,011,169 | 8/1935 | Wappler . |
| 2,022,065 | 11/1935 | Wappler . |
| 2,376,265 | 5/1945 | Meredith . |
| 2,510,205 | 6/1950 | Baird . |
| 2,708,933 | 5/1955 | August .................. 606/45 |
| 2,808,833 | 10/1957 | August . |
| 2,828,747 | 4/1958 | August .................. 606/45 |
| 3,825,004 | 7/1974 | Durden, III .......... 128/275.1 |
| 3,828,780 | 8/1974 | Morrison, Jr. ....... 128/275.1 |
| 3,902,494 | 9/1975 | Haberlen et al. .... 128/275.1 |
| 3,906,955 | 9/1975 | Roberts ............. 128/303.17 |
| 3,911,241 | 10/1975 | Jarrard .................. 200/157 |
| 4,016,881 | 4/1977 | Rioux . |
| 4,021,630 | 5/1977 | Taylor .................. 200/159 |
| 4,040,426 | 8/1977 | Morrison . |
| 4,057,064 | 11/1977 | Morrison . |
| 4,060,088 | 11/1977 | Morrison . |
| 4,307,720 | 12/1981 | Weber, Jr. ............ 128/276 |
| 4,562,838 | 1/1986 | Walker ............... 128/303.14 |
| 4,781,175 | 11/1988 | McGreevy et al. ...... 606/40 |
| 4,882,777 | 11/1989 | Narula . |
| 4,901,719 | 2/1990 | Trenconsky et al. ... 606/49 |
| 4,919,129 | 4/1990 | Weber, Jr. et al. .... 606/49 X |
| 4,920,,980 | 5/1990 | Jackowski . |
| 5,041,110 | 8/1991 | Fleenor .............. 606/40 X |
| 5,088,997 | 2/1992 | Delahuerge et al. ..... 606/42 |
| 5,098,430 | 3/1992 | Fleenor ................ 606/42 |

FOREIGN PATENT DOCUMENTS

| | | |
|---|---|---|
| 57862 | 9/1953 | France .................. 606/45 |
| 1465581 | 12/1966 | France .................. 606/45 |
| 2587258 | 3/1987 | France ............... 219/121.5 |
| 671497 | 5/1952 | United Kingdom . |
| 1014995 | 12/1965 | United Kingdom . |
| 1165148 | 9/1969 | United Kingdom ...... 606/49 |

OTHER PUBLICATIONS

Product brochure from Walker Medical Instruments, Inc., 1829 Lakeview Drive, Portage, Mich. 49081.
Harausgeber, Heinz Kresse, Kompendium Elektromedizin, (Foreword, 14.4 and 14.5) (1978).
Siemens, A. G., Heinz Kresse, Electromedicine Compendium, 2nd revised edition 1978, (Foreword, 14.4 and 14.5).

*Primary Examiner*—Lee S. Cohen
*Attorney, Agent, or Firm*—John R. Ley

[57] ABSTRACT

An electrosurgical handpiece applies electrical energy to a blade electrode to accomplish blade electrosurgery or to a transfer electrode in a nozzle to transfer electrical energy in arcs in a flowing gas to accomplish conductive gas electrocoagulation. The blade electrode may be selectively extended to conduct blade electrosurgery and withdrawn when conductive gas electrocoagulation is accomplished. Finger activated switches on the handpiece control the application of electrical energy to the blade electrode and the application of gas to the nozzle and the electrical energy to the transfer electrode within the nozzle. A cord includes a tubing for supplying gas to the handpiece. The cord also includes a plurality of conductors for conducting electrical energy to the two electrodes and conducting control signals to an electrosurgical apparatus which delivers the electrical energy and the gas. A nozzle and electrode assembly fits within the end of the tubing.

34 Claims, 5 Drawing Sheets

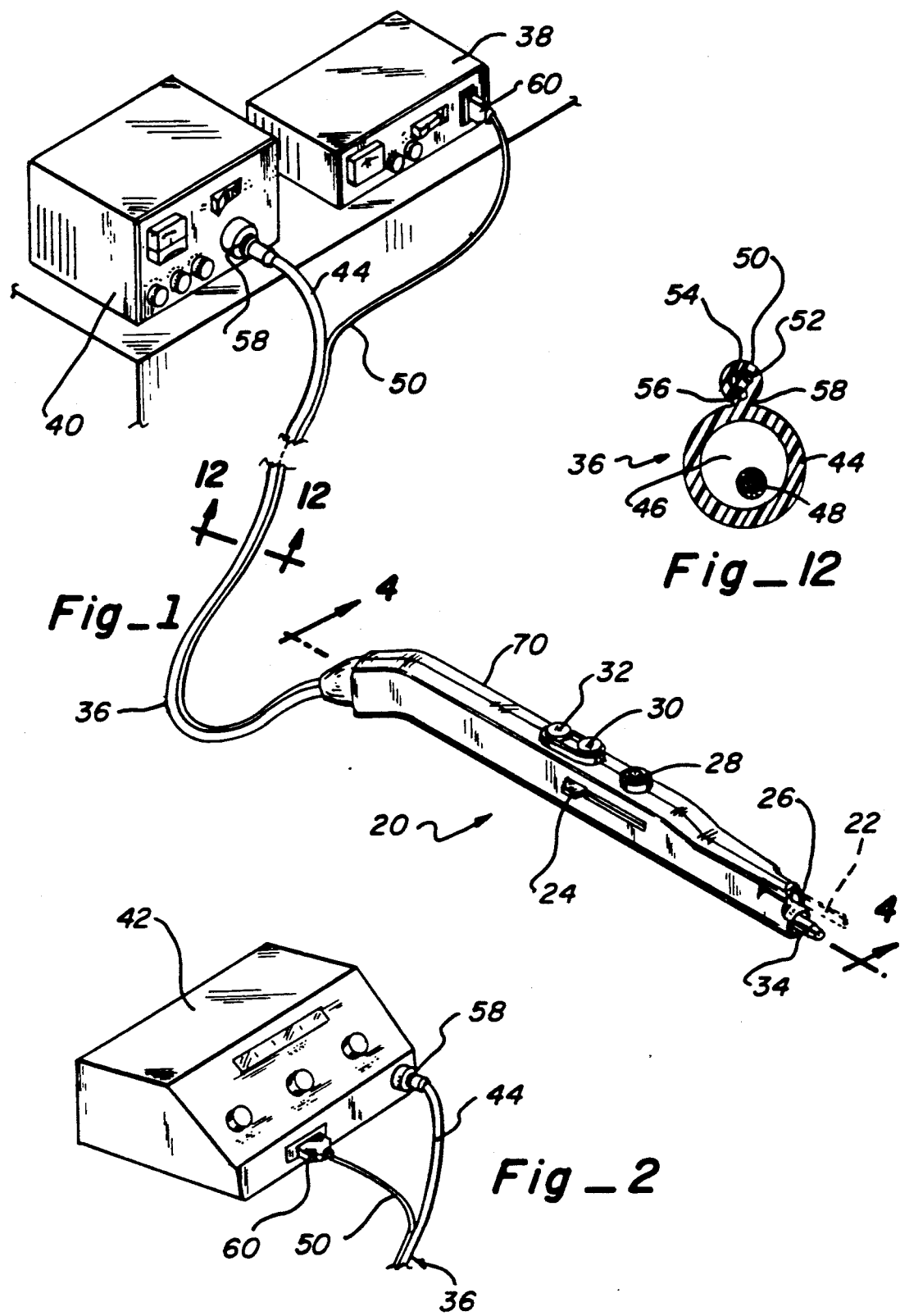

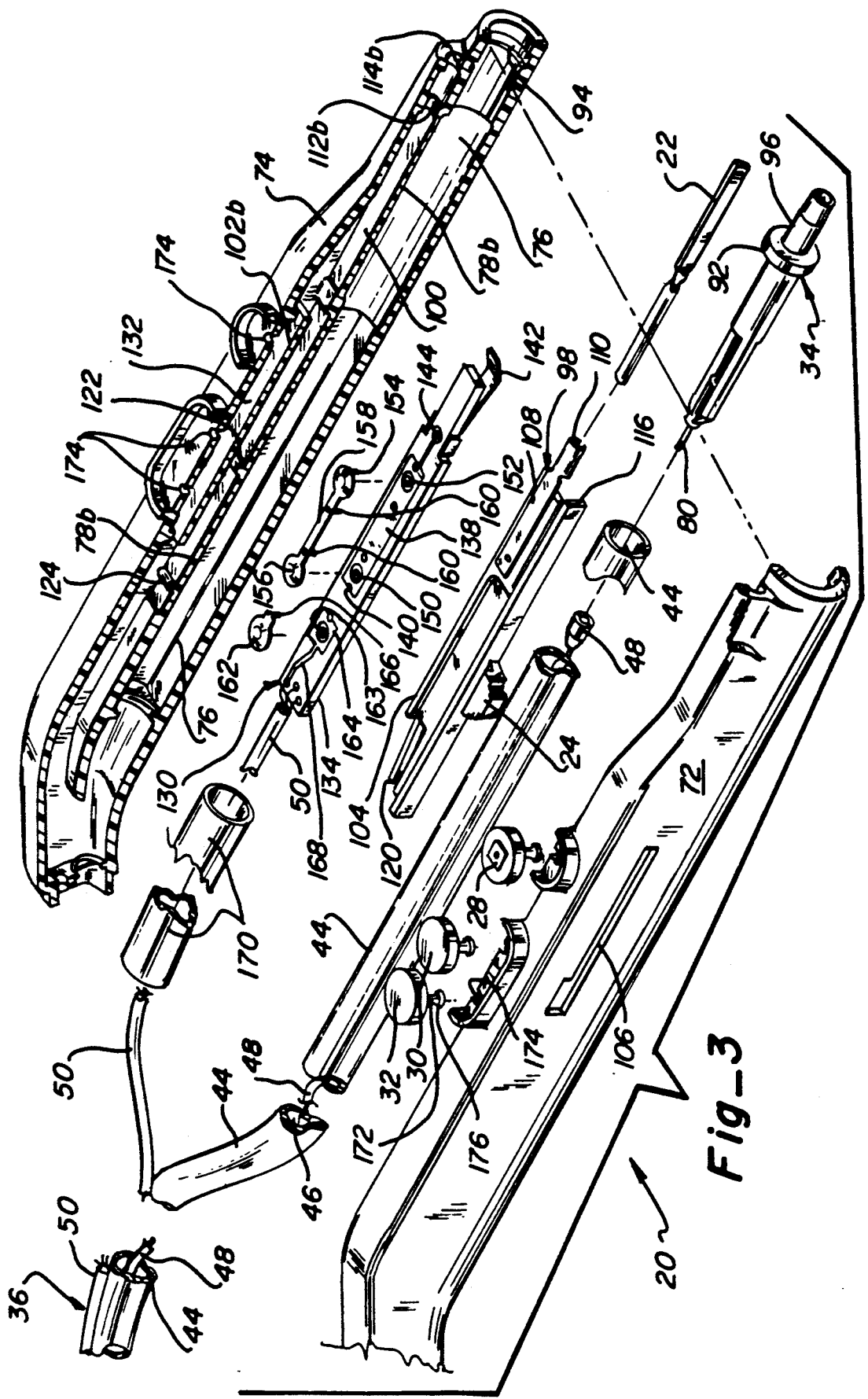

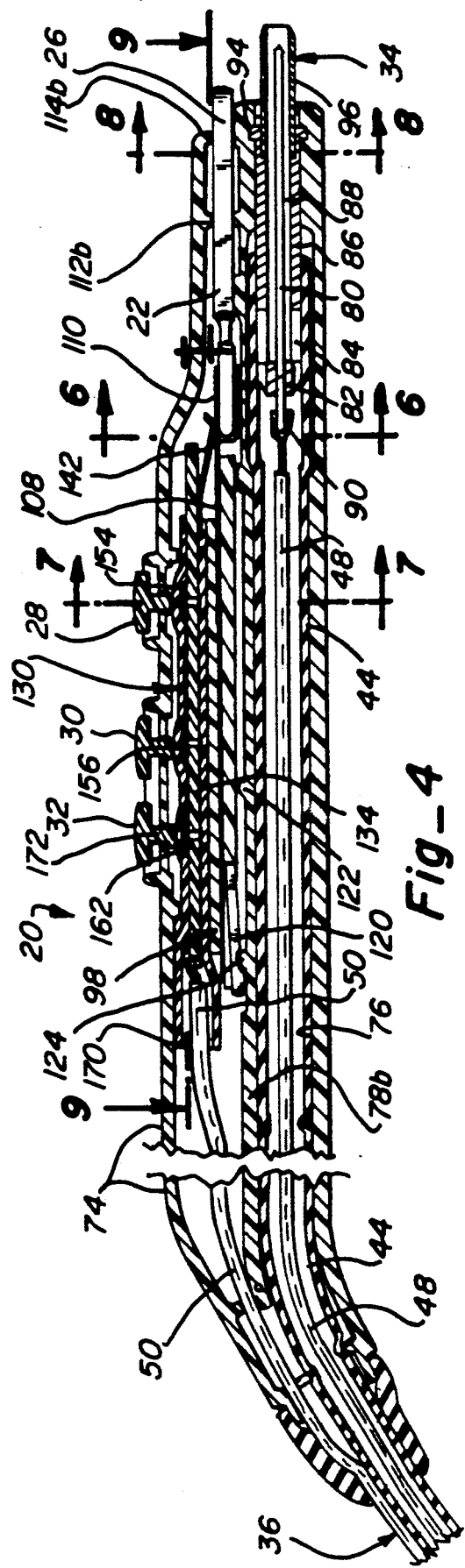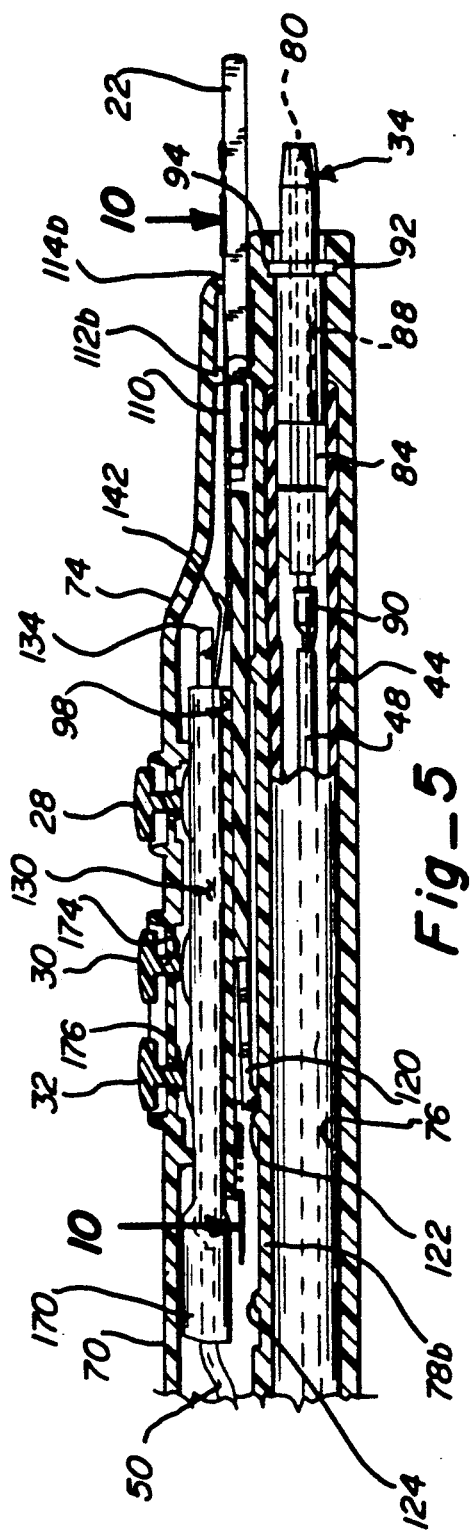

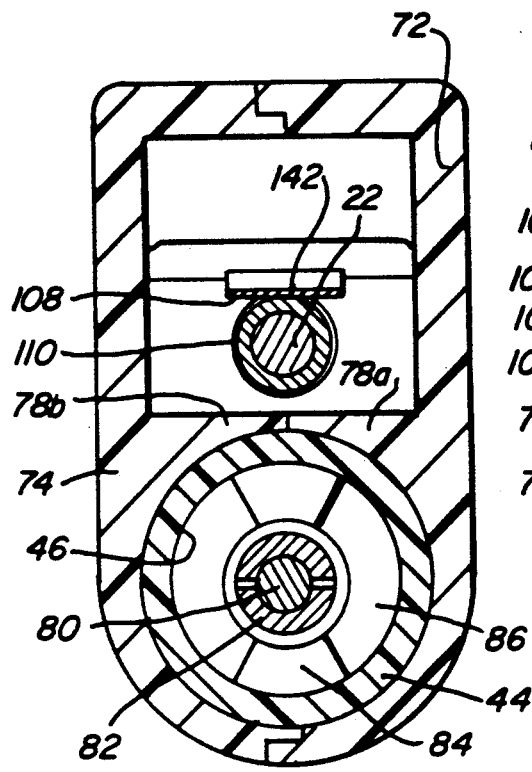
Fig_6
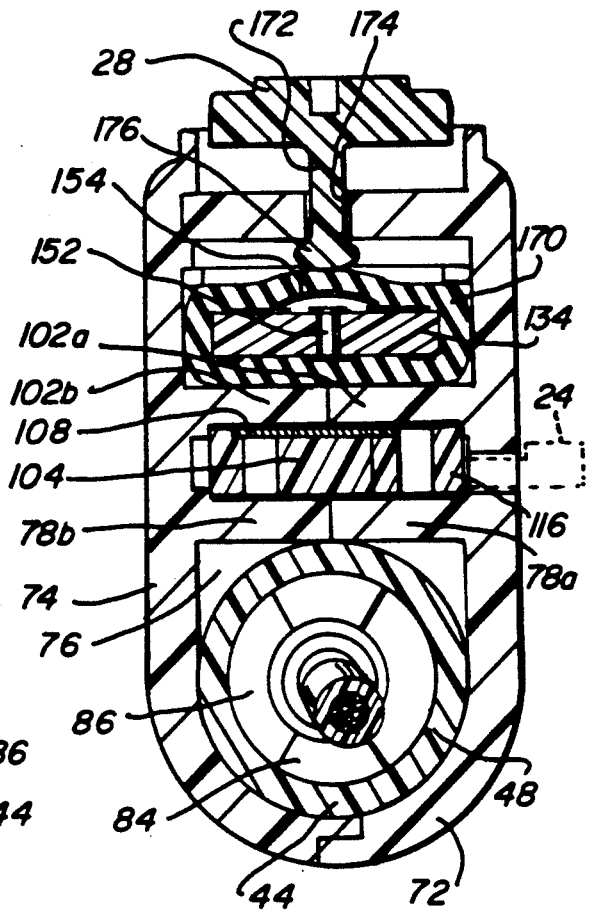
Fig_7
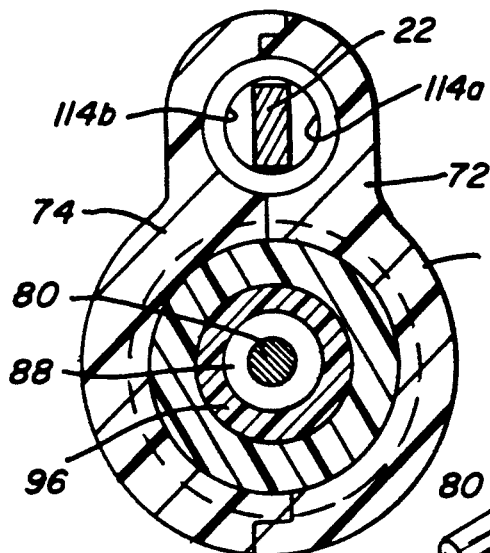
Fig_8
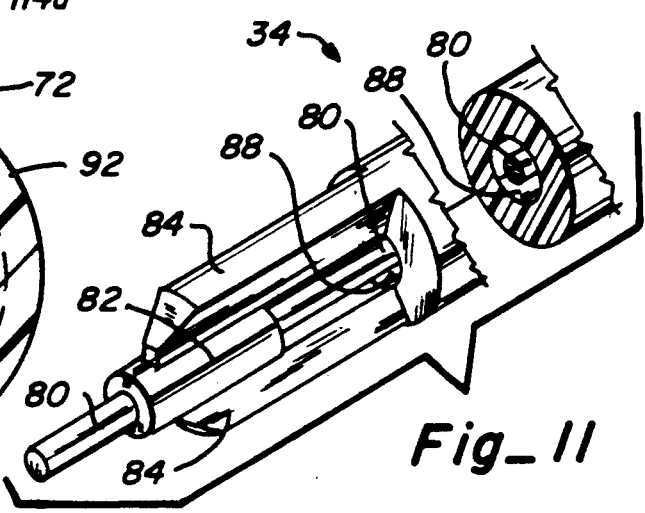
Fig_11

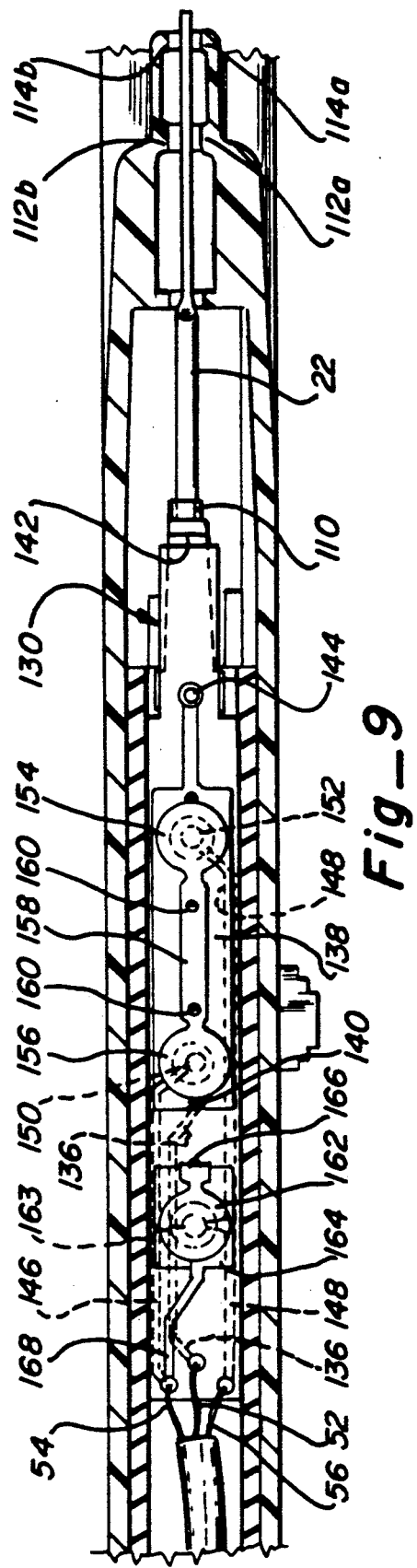
Fig_9
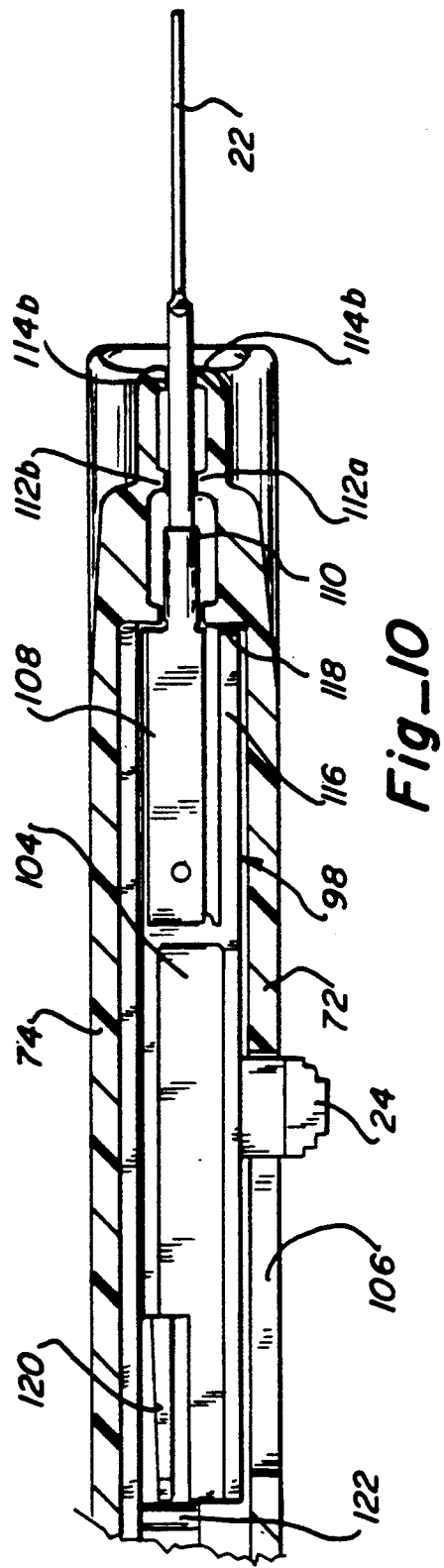
Fig_10

ELECTROSURGICAL HANDPIECE INCORPORATING BLADE AND CONDUCTIVE GAS FUNCTIONALITY

FIELD OF THE INVENTION

This invention pertains to electrosurgery, and more particularly to a new and improved handpiece which incorporates a blade electrode by which to apply electrical energy to the tissue during blade electrosurgery and a nozzle and electrode assembly by which to apply electrical energy in arcs in ionized pathways in a jet of gas flowing to the tissue during conductive gas electrocoagulation.

BACKGROUND OF THE INVENTION

Electrosurgery involves the application of electrical energy to tissue to cut the tissue, coagulate bleeding, or to achieve a combination of cutting and coagulation simultaneously. A high frequency, relatively high powered electrosurgical generator (ESG) supplies the electrical energy, and the energy is applied to the tissue through a blade-like electrode held in a handpiece and manipulated by the surgeon. The blade electrode either contacts the tissue to directly conduct the electrical energy to the tissue, or the blade is slightly spaced from the tissue to create random arcs through the air to the tissue. This type of electrosurgery has been is use for many years, and will be referred to herein as "blade electrosurgery."

To apply the electrical energy to the blade electrode, the ESG is activated or "keyed" by the surgeon depressing a foot switch or by the surgeon depressing finger switches located on the handpiece. When finger switches are used, one switch controls the ESG to supply an energy waveform to achieve cutting, and another switch controls the ESG to supply a different energy waveform to achieve pure coagulation or a blend of cutting and coagulation. The type of waveform delivered in each case is manually selected on the control panel of the ESG. When a foot switch is used, the cutting waveform or the coagulation waveform must be selected for delivery at the control panel of the ESG. A handpiece that separately controls the ESG to obtain both cutting and coagulation effects is desired by many surgeons.

Very recently, a new form of electrosurgery has been introduced. This new form of electrosurgery has been confined to coagulation, and it involves conducting electrical energy to the tissue as arcs in ionized conductive pathways in a flowing stream of inert gas. This type of electrosurgery will be referred to herein as "conductive gas electrocoagulation." Conductive gas electrocoagulation has obtained many significant advancements and improvements in the field of electrosurgery, which prior to its introduction, were impossible and/or unexpected. A more complete description of conductive gas electrocoagulation is available in U.S. Pat. Nos. 4,781,175; 4,901,719; and 4,901,720, all assigned to the assignee of the present invention.

With conductive gas electrocoagulation, the conductive gas jet is delivered to the tissue with a handpiece which the surgeon manipulates. Gas is delivered to the handpiece by a tubing, and an ESG delivers energy to a transfer electrode located within a gas nozzle at the terminal end of the handpiece. The gas flows over the electrode in the nozzle where it is ionized by the electrical potential of the electrode. Electrical energy is transferred from the electrode as arcs in the resulting conductive pathways in the gas flowing to the tissue. In the past, a foot switch has been used to activate the ESG and the flow of gas for conductive gas electrocoagulation.

There are substantial improvements and advantages available from using conductive gas electrocoagulation to coagulate bleeding sites, particularly relatively large, oozing, bleeding sites. However, there are substantial preferences for using blade electrosurgery to cut tissue, primarily because of its ability to simultaneously cut and coagulate. Therefore, many surgeons prefer to use both blade electrosurgery and conductive gas electrocoagulation alternatively during a single surgical procedure. This has required the surgeons to repeatedly change back and forth between the two different handpieces, since cutting and coagulation involves use of a different handpiece than conductive gas electrocoagulation. In addition to using two different types of handpieces, the surgeon may be required to activate each handpiece in a different manner, either by stepping on one foot switch for blade electrosurgery and another foot switch for conductive gas electrocoagulation, or using the foot switch for the conductive gas electrocoagulation and the finger switch on the handpiece for blade electrosurgery.

Changing between the two different handpieces, mentally recognizing that two different activation switches must be operated, and keeping track of both types of equipment, have created additional distractions during surgery which are desireable to avoid. Furthermore, the surgeon has been required to devote additional concentration to the type of equipment rather than to the surgical procedure. Other undesirable factors are also applicable with respect to this situation, and it is against this generally described background that the present invention has resulted.

SUMMARY OF THE INVENTION

Significant aspects of the present invention involve incorporating in a single handpiece, a blade electrode for use in blade electrosurgery, and a nozzle and electrode assembly for applying a conductive gas to the tissue in conductive gas electrocoagulation; locating and providing controls on the handpiece for activating blade electrosurgery and the conductive gas electrocoagulation; applying blade electrosurgery and conductive gas electrocoagulation independently from a single handpiece without interference from the other type of electrosurgery; connecting the handpiece to an electrosurgical apparatus with a cord which includes a tubing in which gas is conducted and which includes conductors which carry electrical energy for electrosurgery and signals for controlling the electrosurgical apparatus; and providing an improved nozzle and electrode assembly which conveniently fits within the end of the tubing.

In accordance with these and other aspects, the handpiece of the present invention includes a housing adapted to be held in the hand of a surgeon during electrosurgery, a blade electrode attached to the housing, a nozzle and electrode assembly attached to the housing and signalling means on the housing for selectively signalling the electrosurgical apparatus to deliver blade electrosurgical energy to the blade electrode and to supply gas to a nozzle and conductive gas electrocoagulation energy to a transfer electrode by which arcs of energy are applied to the gas. Preferably, the signalling means includes a plurality of dome switches connected on a printed circuit board, and the circuit board includes traces which route the signals to the electrosurgical apparatus and electrosurgical energy to the blade electrode. In addition, the blade electrode is preferably moveable to an extended position and to a retracted position, to allow the blade electrode to be retracted during conductive gas electrocoagulation.

In accordance with other aspects of the invention, a cord conducts gas through a tubing to the handpiece and electrical conductors deliver electrosurgical energy to the bade electrode and to the transfer electrode, and other conductors carry signals indicative of the type of electrosurgical energy to be delivered to the handpiece. The cord includes a tubing to which an exterior cable is preferably integrally connected. The tubing defines a conduit through which gas is delivered to the nozzle and electrode assembly. The conductor for delivering electrical energy to the transfer electrode is preferably located within the tubing. The cable preferably includes the conductor for delivering electrosurgical energy to the blade electrode and at least one other conductor for conducting control signals to the electrosurgical apparatus.

In accordance with other aspects of the invention, a nozzle and electrode assembly includes a structure having means adapted to slideably fit within an open end of the tubing which supplies gas to the nozzle, an opening defined in the structure which forces gas supplied from the tubing to flow around the transfer electrode an means connected to the structure for supporting the transfer electrode in a cantilever manner with a substantial forward portion of the electrode exposed to the gas flowing therearound to thereby facilitate transfer of the electrical energy in arcs in conductive pathways in the flowing gas.

A more complete appreciation of the present invention and its scope can be obtained from understanding the accompanying drawings, which are briefly summarized below, the following detailed description of a presently preferred embodiment of the invention, and the appended claims.

BRIEF DESCRIPTION OF THE DRAWINGS

FIG. 1 is a perspective view of a presently preferred embodiment of a handpiece incorporating the present invention, including a cord shown with a portion broken out by which the handpiece is connected to a blade electrosurgery ESG and to a separate conductive gas electrocoagulation apparatus.

FIG. 2 is a perspective view of a single electrosurgical apparatus to which the cord of the handpiece shown in FIG. 1 is connected, in which the functionality of a blade electrosurgery ESG and the conductive gas electrocoagulation apparatus is incorporated.

FIG. 3 is an exploded view of the major components and assemblies of the handpiece shown in FIG. 1.

FIG. 4 is a vertical section side view of the handpiece shown in FIGS. 1 and 3, taken substantially in the plane of line 4—4 of FIG. 1.

FIG. 5 is a partial section view similar to portions of FIG. 4, and further illustrating the blade electrode in an extended position.

FIG. 6 is an enlarged cross section view taken substantially in the plane of line 6—6 of FIG. 4.

FIG. 7 is an enlarged cross section view taken substantially in the plane of line 7—7 of FIG. 4.

FIG. 8 is an enlarged cross section view taken substantially in the plane of line 8—8 of FIG. 4.

FIG. 9 is an enlarged horizontal section view taken substantially in the plane of line 9—9 of FIG. 4.

FIG. 10 is an enlarged horizontal section view taken substantially in the plane of line 10—10 of FIG. 5.

FIG. 11 is an enlarged partial perspective view of a portion of a nozzle and electrode assembly of the handpiece shown in FIG. 3.

FIG. 12 is an enlarged cross section view of the cord connected to the handpiece taken substantially in the plane of line 12—12 of FIG. 1.

DETAILED DESCRIPTION

A presently preferred embodiment of an electrosurgical handpiece for selectively and alternatively delivering electrical energy through a blade electrode to achieve blade electrosurgery and delivering electrical energy in a conductive gas jet to achieve conductive gas electrocoagulation or electrosurgery is generally shown in FIG. 1, and may be thought of as a "dual function" handpiece 20.

The handpiece 20 includes a conventional blade electrode 22 which is moveable by means of moving a slider 24 on the exterior of the handpiece 20. When the slider 24 is in the rear position, the blade electrode 22 is retracted, leaving only the forward tip 26 thereof exposed at the front end of the handpiece. When the slider 24 is moved forward, the blade electrode 22 is extended to the extended position shown by the phantom lines in FIG. 1. In the extended position, the blade electrode 22 is used for applying electrical energy to the tissue to achieve blade electrosurgery. Means for controlling the application of cutting and coagulation energy to the blade electrode 22 are activated by the surgeon depressing buttons 28 and 30, respectively, by finger pressure. When the blade electrode 22 is not used for blade electrosurgery, preferably the slider 24 is moved to the rearward position thereby retracting the blade electrode 22 and leaving only its forward tip 26 exposed. To achieve conductive gas electrocoagulation, a button 32 is depressed. A stream of ionized gas which conducts arcs of electrical energy is delivered from a nozzle and electrode assembly 34 located in the forward end of the handpiece 20.

With the blade electrode 22 in its extended position, it extends sufficiently forward from the front end of the handpiece 20 to contact the tissue without interference from the nozzle and electrode assembly 34. When the blade electrode 22 is withdrawn to the retracted position, the forward end of the blade electrode 22 extends no farther forward than the nozzle and electrode assembly 34 and the conductive gas jet is delivered without interference from the blade electrode 22. Although not presently expected, some surgical procedures might allow the blade electrode to remain extended or partially extended while the conductive gas jet is applied.

A cord 36 connects the handpiece 20 to a separate ESG 38 and a conductive gas electrocoagulation apparatus 40 as shown in FIG. 1, or to a single device 42 which incorporates an ESG and the conductive gas electrocoagulation apparatus as shown in FIG. 2. The device 42 is capable of delivering electrical energy to the blade electrode, and electrical energy and gas, preferably inert gas, to the electrode of the nozzle and electrode assembly 34. The single device 42 includes the capability of distinguishing the circumstances and type of electrical energy to deliver based on signals resulting from depression of the buttons 28, 30 and 32 on the handpiece 20, but separate interrogation circuitry may be needed to separately control the ESG 38 and the apparatus 40 when separately used as shown in FIG. 1. The apparatus represented at 38, 40 and 42 is referred to herein as "electrosurgical apparatus".

The preferred form of the cord 36 is shown in greater detail in FIG. 12. The cord 36 is generally formed by a flexible, electrically-insulating material which defines a tubing 44 that has an inner conduit 46 for conducting the inert gas to the handpiece for conductive gas electrosurgery. An insulated electrical conductor 48 is located within the conduit 46 through which electrical energy for conductive gas electrocoagulation is supplied to the handpiece. The conductor 48 will be referred to herein as the "CGE conductor".

The material from which the cord is formed also defines a cable 50 within which three separate conductors 52, 54 and 56 are located. The cable 50 is integrally joined to the tubing 44 at a neck 58 by the insulating material of the cord. The conductor 52 conducts electrical energy to the handpiece for blade electrosurgery, and will be referred to herein a the "BE conductor." The conductors 54 and 56 conduct control signals to which are interpreted to control the flow of gas and the type of electrical energy delivered over the CGE and BE conductors 48 and 52, respectively, to the handpiece to achieve conductive gas electrocoagulation and blade electrosurgery. Control signals appear on the conductors 54 and 56 by the closure of switches activated by the buttons (28, 30, 32, FIG. 1) of the handpiece. The control signals may be interpreted by a variety of different interrogation circuits to obtain conductive gas electrocoagulation or blade electrosurgery.

The tubing 44 and the cable 50 may be separated at the neck 58 to allow the three conductors 52, 54 and 56 and the tubing 44 and the CGE conductor 48 to be routed to separate locations within the handpiece as is shown in FIG. 3. Similarly at the other end of the cord 36, the tubing 44 and the cable 50 may be separated, with the tubing 44 connected through a connector 58 to the electrosurgical apparatus. The connector 58 conducts both the gas to the conduit 46 and electrical energy to the CGE conductor 48. A connector 58 suitable for this purpose is disclosed in U.S. Pat. Nos. 4,781,175 and 4,901,719. The conductors 52, 54 and 56 of the cable 50 are connected to the electrosurgical generator 38 or device 42 by a conventional connector 60 (FIGS. 1 and 2).

A housing 70 for the handpiece 20 includes two housing members 72 and 74 within which all of the other components and assemblies of the handpiece 20 are retained and contained. FIG. 3 illustrates these components and assemblies. The housing members 72 and 74 are joined together during assembly of the handpiece 20. The housing members 72 and 74 are preferably formed of plastic material, and are preferably joined together by ultrasonically welding along their mating surfaces.

The lower portion of the housing 70 is formed into a channel 76 within which the tubing 44, the CGE conductor 48 and the nozzle and electrode assembly 34 are located, as is shown in FIGS. 3 to 5 and 7. The channel 76 is formed by two walls 78a and 78b (FIG. 7) which extend inwardly from the housing members 72 and 74 respectively. The walls 78a and 78b contact each other when the housing members 72 and 74 are joined together. The tubing 44 and CGE conductor 48 extend along the channel 76 and connect to the nozzle and electrode assembly 34 which is connected and retained at the forward end of the channel 76.

As is shown in FIGS. 3 to 6, 8 and 11, the nozzle and electrode assembly 34 includes a metallic transfer electrode 80 which is retained in a cantileverly supported manner at its rearward end by a support collar 82. Ribs 84 connect the support collar 82 to a cylindrical structure 86. A center opening 88 extends in the cylindrical structure 86 and surrounds the electrode 80. The tubing 44 fits over the rearward end of the cylindrical structure 86. The cylindrical structure 86 is one example of means for slip fitting or slideable insertion within the conduit 46, since other structures and configurations could also be employed. The CGE conductor 48 is connected to the rearward end of the electrode 80 by a connector 90 (FIG. 4). A flange 92 extends radially outwardly from the structure 86 and is retained in semicircular grooves 94 formed in the housing members 72 and 74. The flange 92 and the grooves are an example of means for holding the nozzle and electrode assembly 34 within the housing 70.

A ceramic sleeve 96 (FIGS. 4 and 8) is retained within the structure 86 and surrounds the forward exposed end of the electrode 80. The interior of the ceramic sleeve 96 continues to define the opening 88 at least to the forward end of the electrode 80 and preferably slightly beyond. The gas in the tubing 44 enters the opening 88 around the ribs 84 and flows forward along the exposed electrode 80. The opening 88 in the structure 86 and the sleeve 96 defines a nozzle to direct the conductive gas delivered from the assembly 34 in a laminar flow to the tissue. As the gas flows forward around the exposed electrode 80, the voltage of the electrical energy supplied to the electrode 80 ionizes the gas. Arcs of electrical energy are transferred from the electrode in conductive pathways to the tissue while the gas clears blood and fluid from the tissue surface. The conductive gas electrocoagulation effect is more completely described in U.S. Pat. Nos. 4,781,175; 4,901,719 and 4,901,720. In some types of handpieces in which the nozzle and electrode assembly 34 is used, the tubing may be rigid and also essentially form a housing for the handpiece. Slip fitting the structure 86 into the end of the tubing achieves relatively convenient assembly of the handpiece, and the structure may be easily retained to the tubing by an adhesive if desired.

Separating the cord 36 at the neck 58 allows for the relatively convenient and efficient implementation of the conductive gas electrocoagulation aspects of the handpiece 20 separately from the blade electrosurgical aspects within the handpiece 20.

A blade electrode support assembly 98 (FIG. 3) of the handpiece 20 is also slideably positioned within the housing 70 in a longitudinal space 100 defined by the abutting pairs of channel walls 78a and 78b on the bottom, and another pair of abutting channel walls 102a and 102b (FIG. 7) which protrude inwardly from the housing members 72 and 74, respectively. The blade support assembly 98 includes a base member 104 which moves longitudinally within the space 100. The slider 24 is part of the base member 104 and extends to the exterior of the housing 70 through a slot 106 formed in the housing member 72, as is shown in FIGS. 3 and 10. Finger pressure on the slider 24 moves the base member 104 forwardly and rearwardly within the space 100 in the housing 70. Preferably, the base member 104 is made of plastic. Support means other than the assembly 98 can achieve a variety of configurations.

A flat metallic sheet conductor 108 is preferably insert molded, or otherwise attached, to the forward end of the base member 104 (FIGS. 3-5 and 10). The blade electrode 22, which is of the conventional configuration, is connected to the sheet conductor 108 at the forward end of the base member 104 by a metallic collet 110. The rear end of the blade electrode 22 is cylindrical in configuration and is frictionally inserted into the collet 110, to retain the blade electrode 22 in position. This frictional fit allows replacement of the blade electrode and the connection of different types of blade electrodes, such as a needle electrode. As is shown in FIGS. 4, 5, and 8 to 10, semicircular surfaces of inward protruding walls 112a and 112b and outside semicircular surfaces 114a and 114b of the housing members 72 and 74 respectively, define cylindrical support surfaces at the forward end of the space 100 to support the blade electrode 22 when it is extended. Support for the blade electrode 22 in this manner allows it to be firmly manipulated with movement of the handpiece 20.

The base member 104 includes a forward projecting tang 116 which slides along the inner surface of the housing member 72, as shown in FIG. 10. The maximum forward extent of movement of the base member 104, and consequently the blade electrode 22, is defined upon the forward end of the tang 116 abutting a shoulder 118 of the housing member 72. Another tang 120 extends rearwardly of the base member 104. The rearward tang 120 is resiliently biased downwardly and snaps over a forward ridge 122 to hold the base member in the forward position (FIG. 5). Similarly the tang 120 snaps over a rear ridge 124 formed in the walls 78a and 78b to hold the base member in a retracted position. The ridges 122 and 124 are one example of a variety of structures formed in the housing which can achieve this retention function in conjunction with the tang.

A switch assembly 130 is also located in the housing 70, in an area 132 formed by the walls 102a and 102b (FIG. 7) and upper top portions of the housing members 72 and 74 as is shown in FIGS. 3 to 5. The switch assembly 130 preferably includes a printed circuit board 134 to which the conductors 52, 54 and 56 are soldered at the rearward end. Traces formed on the top and bottom surfaces of the printed circuit board 134 route the electrical signals to the components of the switch assembly 130.

A trace 136 connects the BE conductor 52 to a metallic switch plate 138 at a through hole 140, as is shown in FIG. 9. The plate 138 is attached to the top surface of the board 134. A metallic tongue 142 is connected to the forward end of the printed circuit board 134 and to the switch plate 138 by a rivet 144 (FIGS. 3 and 9). The tongue member 142 extends downward from the printed circuit board and contacts and slides against the sheet conductor 108 of the support assembly 98, as is shown in FIGS. 4 and 5. Blade electrosurgical energy is transferred from the BE conductor 52 to the trace 136, to the switch plate 138, to the tongue member 142, and to blade electrode 22.

The other two signal conductors 54 and 56 are respectively connected to the traces 146 and 148, as shown in FIG. 9. The forward ends of the traces 146 and 148 are connected to through holes 150 and 152, respectively. A pair of snap-type dome switches 154 and 156 are connected to the switch plate 138 in positions above the through holes 150 and 152, respectively.

The dome switches 154 and 156 are connected together by a metallic bridge 158, thereby allowing the dome switches 154 and 156 to be formed from a single piece of metallic material. The bridge 158 is held in place on the switch plate 138 by alignment stakes 160 (FIG. 3). Upon depression of the dome switch 154, the signal from the BE conductor 52 on the switch plate 138 is conducted to the through hole 152 to the trace 148 and to the conductor 56. Depression of the dome switch 156 conducts an electrical signal from the BE conductor 52 on the switch plate 138 to the through hole 150 to the trace 146 to the other conductor 54. In this manner, control signals are supplied to the ESG to control it either to deliver cutting blade electrosurgical energy to the blade electrode 22, or to deliver coagulation electrosurgical energy to the blade electrode 22.

A third dome switch 162 is located on the upper side of the printed circuit board 134. The dome switch 162 is connected to an auxiliary switch plate 164 by a stake 166. The switch plate 164 is connected by a trace 168 to the through hole where the conductor 54 is connected to the printed circuit board 134. A through hole 163 is formed in the circuit board 134 beneath the dome switch 162 and is connected to the trace 148. Depression of the dome switch 162 connects the two traces 168 and 148, thereby connecting the conductors 54 and 56. A sensing circuit, not shown, will sense the connection of the conductors 54 and 56 to control the conductive gas electrocoagulation apparatus. In general, a separate signal will be supplied to one of the conductors 54 or 56, and that signal will be sensed on the other conductor, to control the activation of the conductive gas electrocoagulation apparatus. The signal supplied on the conductor to activate the conductive gas electrocoagulation apparatus is separate and distinct from the electrical signal supplied on the BE conductor 52 and which is conducted back through one of the conductors 54 or 56 when one of the dome switches 154 and 156 is depressed to activate the blade electro-surgical apparatus.

The switch assembly is one example of signalling means for selectively signalling the electrosurgical apparatus to supply blade electrosurgical energy to the blade electrode and to supply conductive gas electrocoagulation energy to the nozzle and transfer electrode. There are a variety of other devices and arrangements which are capable of developing control signals for controlling the electrosurgical apparatus in the manner described.

An insulating sleeve 170 completely surrounds the switch assembly 130, except that the forward end of the tongue member 142 is exposed for electrical and mechanical contact with the sheet conductor 108 of the support assembly 98 (FIGS. 4, 5 and 7). The rear portion of the sleeve extends over the front end of the cable 50 (FIG. 5).

The three buttons 28, 30 and 32, are one example of means for activating or depressing the dome switches 154, 156 and 162. The buttons 28, 30 and 32 each include a downwardly extending shaft 172. The shaft 172 extends downward from each of the buttons through an opening 174 defined in the upper surface of the housing 70 by semicircular facing indentions formed in the abutting mating surfaces of the housing members 72 and 74, as is shown in FIG. 7. A lower expanded end 176 of the shaft 172 is located within the interior of the housing 70. The enlarged end 176 retains the buttons 28, 30 and 32 to the housing once the housing members 72 and 74 are joined. As an alternative instead of the housing members joining together at the openings 174, an integral button mounting flange having the openings therein may extend completely across the space beneath the buttons between the housing members. In this case the enlarged ends 176 of the shafts 172 are pressed through the openings to retain the buttons to the housing.

Each enlarged end 176 of a button is located directly above a dome switch. The sleeve 170 separates the enlarged end 176 from the dome switch. Upon depression of a button, the enlarged end 176 moves downward, compressing the sleeve and deflecting the dome switch inwardly. The dome switch makes contact with the center through hole, and causes a signal to be supplied to one of the two conductors 54 or 56, thereby signalling the electrosurgical apparatus to deliver the electrosurgical effect indicated by depressing the particular button.

The handpiece 20 thus obtains the very desirable benefit of integrating a conventional blade electrode with a conductive gas nozzle and electrode assembly in a single handpiece, thereby allowing the selective delivery of either conventional cutting and coagulation electrosurgery current through a blade electrode, or the delivery of conductive gas electrocoagulation energy through a stream of ionized conductive inert gas. Furthermore, either type of electrosurgical effect may be readily selected by activating the buttons or switches on the handpiece. In addition, the handpiece provides the ability to control conductive gas electrocoagulation by manipulating a control switch or button on the handpiece itself. Many other advantages and improvements are available from the handpiece 20.

A presently preferred embodiment of the present invention and many of its improvements have been described with a degree of particularity. It should be understood that this description has been made by way of preferred example, and that the invention is defined by the scope of the following claims.

The invention claimed is:

1. A handpiece for applying electrical energy from an electrosurgical apparatus to tissue during electrosurgery, comprising:
    a housing adapted to be held in the hand of a surgeon during electrosurgery;
    a blade electrode attached to the housing;
    a nozzle and electrode assembly attached to the housing and including a nozzle for conducting gas and a transfer electrode positioned within the nozzle by which to transfer electrical energy to gas; and
    signalling means attached to the housing and operative for selectively signalling the electrosurgical apparatus to supply blade electrosurgical electrical energy to the blade electrode and to supply gas to the nozzle and conductive gas electrocoagulation energy to the transfer electrode.

2. A handpiece as defined in claim 1 wherein the signalling means further comprises:
    first switch means for signalling the electrosurgical apparatus to supply cutting blade electrosurgical energy to the blade electrode;
    second switch means for signalling the electrosurgical apparatus to supply coagulation blade electrosurgical energy to the blade electrode; and
    third switch means for signalling the electrosurgical apparatus to supply conductive gas electrocoagulation energy to the transfer electrode and to supply gas to the nozzle.

3. A handpiece as defined in claim 2 further comprising:
    a printed circuit board to which the first, second and third switch means are connected.

4. A handpiece a defined in claim 3 wherein the first, second and third switch means each comprise a dome switch connected to the printed circuit board.

5. A handpiece as defined in claim 1, further comprising:
    means for selectively extending and retracting the blade electrode.

6. A handpiece as defined in claim 5 wherein:
    the blade electrode occupies a retracted position when retracted and extended position when extended; and
    the blade electrode extends substantially beyond a forwardmost end of the nozzle when extended and extends no further forward than approximately the forward end of the nozzle when retracted.

7. A handpiece as defined in claim 1 further comprising:
    a support assembly movably supported within the housing and to which the blade electrode is connected; and
    a slider connected to the support assembly and positioned at the exterior of the housing by which to move the support assembly and the connected blade electrode.

8. A handpiece as defined in claim 1 for use with a tubing connected to the handpiece for delivering gas from the electrosurgical apparatus to the handpiece, wherein the nozzle and electrode assembly further comprises:
    a structure adapted to be received within an end of the tubing at the handpiece;
    an opening defined by the structure within which the transfer electrode extends and through which the gas flows along the transfer electrode; and
    means connected to the structure for supporting the transfer electrode at a rear end thereof in a cantilever manner to extend the transfer electrode forward through the opening.

9. A handpiece as defined in claim 8 for use with a conductive gas electrical conductor for conducting conductive gas electrocoagulation energy from the electrosurgical apparatus to the handpiece, and wherein the tubing defines a conduit through which the gas flows and the conductive gas electrical conductor is located in the conduit, the handpiece further comprising:
    means connected to the rear end of the transfer electrode and operative for electrically connecting the conductive gas electrical conductor to the rear end of the transfer electrode at a position adapted to be within the conduit.

10. A handpiece as defined in claim 1 for use with a tubing having a conduit for delivering gas from the electrosurgical apparatus to the handpiece, and with a conductive gas electrical conductor positioned within the conduit for delivering electrical energy from the electrosurgical apparatus to the handpiece, and with a blade electrosurgical conductor located outside the tubing for delivering electrical energy from the electrosurgical apparatus to the handpiece, the handpiece further comprising:
    means connected to the nozzle and electrode assembly for insertion within the conduit at the housing;

means for connecting the transfer electrode to the conductive gas electrical conductor within the conduit at the housing; and means for connecting the blade electrosurgical conductor to the signalling means within the handpiece at a location separated from the tubing.

11. A handpiece including a blade electrode for applying cutting and coagulation blade electrical energy from an electrosurgical apparatus to tissue by which to perform blade cutting and coagulation electrosurgery, a nozzle and a transfer electrode for respectively applying gas and electrical energy from an electrosurgical apparatus to tissue by which to perform conductive gas electrocoagulation, and control means for controlling the application of electrical energy and gas to achieve conductive gas electrocoagulation in selective alternation with blade cutting and coagulation electrosurgery; and a cord in combination with the handpiece for supplying the electrical energy and gas to the handpiece, the cord comprising:

a tubing defining an interior conduit through which gas is supplied to the nozzle of the handpiece;

a conductive gas electrical conductor extending within the conduit and connected to the transfer electrode by which electrical energy is supplied to the transfer electrode;

a cable attached at the exterior of the tubing and including a plurality of electrical conductors, one of the conductors in the cable connected to the blade electrode for conducting blade electrical energy to the blade electrode and at least one other of the conductors in the cable connected to the control means for carrying a signal from the handpiece to the electrosurgical apparatus to control the electrosurgical apparatus to supply blade electrical energy to the conductor connected to the blade electrode or to supply electrical energy to the transfer electrode and gas to the conduit and nozzle.

12. An invention as defined in claim 11 wherein the conductive gas electrical conductor is positioned within the conduit and extends along the length of the tubing.

13. An invention as defined in claim 12 wherein the transfer electrode connects to the conductive gas electrical conductor within the conduit.

14. An invention as defined in claim 12 wherein the cable is integrally attached to the tubing at a neck formed of the same material from which the tubing is formed.

15. An invention as defined in claim 14 wherein the cable and the tubing are separable at the neck by severing the neck material.

16. An invention as defined in claim 15 wherein the handpiece further includes a housing, a switch assembly positioned within the housing, means for retaining the nozzle and transfer electrode within the housing at a position separate from the location of the switch assembly, means extending to the exterior of the housing and operative for activating the switch assembly, the cable and the tubing are severed at the neck within the housing and routed separately within the housing to the blade electrode and to the nozzle and transfer electrode, and the control means includes the switch assembly.

17. An invention as defined in claim 16 wherein the conductive gas electrical conductor connects to the transfer electrode within the conduit.

18. Apparatus for applying gas and electrical energy from an electrosurgical apparatus to perform conductive gas electrocoagulation, comprising:

a tubing which defines an interior conduit through which gas is supplied from the electrosurgical apparatus;

an electrical conductor extending along the tubing which conducts electrical energy from the electrosurgical apparatus;

a nozzle and electrode assembly which comprises an elongated transfer electrode, a structure defining an elongated opening, a portion of the opening defining a nozzle, the structure including means for supporting the transfer electrode at a rear end thereof in a cantilever manner to extend the transfer electrode forward through the opening and to substantially expose the majority of the transfer electrode, the structure slip fitting within an end of the tubing, the gas supplied through the conduit being forced to flow in the opening and around the substantially exposed forward majority of the electrode when the structure is positioned within the end of the tubing, the cantilever supporting means further being located in the conduit when the structure is positioned within the end of the tubing;

means located in the conduit for electrically connecting the rear end of the transfer electrode and the electrical conductor at a location within the conduit.

19. Apparatus as defined in claim 18 further comprising:

a ceramic sleeve defining a part of the opening and surrounding a majority of the exposed portion of the electrode and extending to a forward location at least equal to the forwardmost extent of the electrode.

20. A handpiece for applying cutting and coagulation blade electrical energy from an electrosurgical apparatus to a patient by which to perform blade cutting and coagulation electrosurgery and for selectively alternatively applying gas and electrical energy from the electrosurgical apparatus to the patient by which to perform conductive gas electrocoagulation, the handpiece adapted to be connected to the electrosurgical apparatus by a cord, the cord including a tubing adapted to extend into the handpiece for supplying gas to a forward end of the tubing, the cord further including an electrical conductor means for supplying electrical energy to the handpiece, the handpiece comprising:

a housing adapted to be held in the hand of a surgeon during electrosurgery and electrocoagulation;

a blade electrode attached to the housing by which to perform blade cutting and coagulation electrosurgery;

supporting means for supporting the blade electrode at the housing for movement between an extended position wherein a portion of the blade electrode extends beyond a forward end of the housing and a retracted position wherein a substantial majority of the blade electrode is retracted within the housing;

slider means connected to the supporting means and extending to the exterior of the housing, the slider means moving the supporting means to position the blade electrode in the extended and retracted positions;

a nozzle and electrode assembly attached to the housing by which to perform conductive gas electrocoagulation, the nozzle and electrode assembly including means defining a nozzle and a transfer electrode positioned within the nozzle, the nozzle and electrode assembly including a structure adapted to fit within the forward end of the tubing and including an opening communicating with the nozzle, the structure forcing the gas supplied in the tubing to flow through the opening and around the transfer electrode prior to exiting the nozzle;

signalling means attached to the housing and operative for selectively signalling the electrosurgical apparatus to supply blade electrosurgical electrical energy to the blade electrode and to supply gas and conductive gas electrocoagulation energy to the nozzle and transfer electrode; and activation means on the exterior of the housing and operative for activating the signalling means.

21. A handpiece as defined in claim 20 wherein the signalling means further comprises:
first switch means for signalling the electrosurgical apparatus to supply cutting blade electrosurgical energy to the blade electrode;
second switch means for signalling the electrosurgical apparatus to supply coagulation blade electrosurgical energy to the blade electrode; and
third switch means for signalling the electrosurgical apparatus to supply conductive gas electrocoagulation energy to the transfer electrode and to supply gas to the nozzle.

22. A handpiece as defined in claim 21 further comprising:
a printed circuit board to which the first, second and third switch means are connected, and wherein:
the first, second and third switch means each include a dome switch.

23. A handpiece as defined in claim 22 further comprising:
a sheet conductor attached to the supporting means, the sheet conductor conducting electrical energy to the blade electrode; and
a tongue member connected to the printed circuit board, the tongue member electrically contacting the sheet conductor to conduct electrical energy to the blade electrode as the supporting means moves to the extended position.

24. A handpiece as defined in claim 23 wherein the cord includes a plurality of electrical conductors, a first one of which supplies blade electrosurgical energy to the handpiece, and a second one of which supplies a signal to control the electrosurgical apparatus, and further:
the printed circuit board includes a first trace to which one of the dome switches is connected and to which the first conductor of the cord is connected and to which the tongue member is connected, and a second trace with which the one dome switch makes electrical contact when deflected and to which the second conductor is connected.

25. A handpiece as defined in claim 20, wherein:
the transfer electrode has an elongated configuration, the opening defined in the structure being elongated, and further including means connected to the structure for supporting the transfer electrode at a rear end thereof in a cantilever manner to extend forward through the opening and to substantially expose a majority of the transfer electrode within the opening, the structure adapted to fit within the forward end of the tubing to force gas supplied from the tubing to flow around the substantially exposed forward majority of the transfer electrode, the opening being a part of the nozzle.

26. A handpiece as defined in claim 20 wherein the supporting means further comprises:
a longitudinally projecting tang which is resiliently biased to contact a portion of the housing; and
at least one deflection structure of the housing which contacts and deflects the tang upon movement of the supporting means to position the blade electrode in one of the extended or retracted positions, the deflection of the tang against the deflection structure retaining the supporting means in position.

27. A handpiece as defined in claim 26 further including two of said deflection structures, one of the deflection structures and the tang operatively retain the supporting means in the position to support the blade electrode in one of the extended or retracted positions, and the other of the deflection structures and the tang operatively retain the supporting means in the position to support the blade electrode in the other of the extended or retracted positions.

28. A handpiece for applying electrical energy from an electrosurgical apparatus to tissue during electrosurgery, comprising:
a housing adapted to be held in the hand of the surgeon during electrosurgery;
a blade electrode attached to the housing;
a nozzle and electrode assembly attached to the housing and including a nozzle for conducting inert gas and a transfer electrode positioned within the nozzle by which to transfer electrical energy to the inert gas;
first switch means attached to the handpiece for signalling the electrosurgical apparatus to supply cutting blade electrosurgical energy to the blade electrode; and
second switch means attached to the handpiece for signalling the electrosurgical apparatus to supply coagulation blade electrosurgical energy to the blade electrode.

29. An apparatus for applying gas and electrical energy from an electrosurgical apparatus to conduct electrosurgery, comprising:
a handpiece adapted to be held in the hand of a surgeon during electrosurgery;
means attached to the handpiece for conducting blade electrosurgery;
means attached to the handpiece for conducting conductive gas electrocoagulation;
first signalling means adapted to be electrically connected to the electrosurgical apparatus and operative for selectively signalling the electrosurgical apparatus to supply either cutting or coagulation blade electrosurgical energy to the blade electrosurgery conducting means; and
second signalling means adapted to be electrically connected to the electrosurgical apparatus and operative for signalling the electrosurgical apparatus to supply inert gas and conductive gas electrocoagulation energy to the conductive gas electrocoagulation conducting means.

30. An apparatus as defined in claim 29 wherein the first signalling means further comprises:
first switch means for signalling the electrosurgical apparatus to supply cutting blade electrosurgical energy to the blade electrosurgery means; and second switch means for signalling the electrosurgical apparatus to supply coagulation blade electrosurgical energy to the blade electrosurgery means.

31. An apparatus as defined in claim 30 wherein the first and second switch means are attached to the handpiece.

32. A method of alternately conducting blade electrosurgery or conductive gas electrocoagulation from a handpiece, comprising:

forming on the handpiece, means for applying blade electrosurgery or conductive gas electrocoagulation from the handpiece;

operatively interconnecting the handpiece with an electrosurgical apparatus which is capable of supplying blade electrosurgery electrical energy to conduct blade electrosurgery or conductive gas electrocoagulation electrical energy and inert gas to conduct conductive gas electrocoagulation;

signalling the electrosurgical apparatus to supply one of either cutting or coagulation blade electrosurgical energy to the handpiece for blade electrosurgery; and alternately signalling the electrosurgical apparatus to supply inert gas and conductive gas electrocoagulation energy to the handpiece for conductive gas electrocoagulation.

33. A method as defined in claim 32 wherein the steps of signalling the electrosurgical apparatus further comprise:

delivering a first signal to signal the electrosurgical apparatus to supply cutting blade electrosurgical energy to the handpiece;

delivering a second signal to signal the electrosurgical apparatus to supply coagulation blade electrosurgical energy to the handpiece; and delivering a third signal to signal the electrosurgical apparatus to supply inert gas and conductive gas electrocoagulation energy to the handpiece.

34. A method as defined in claim 33 further comprising:

originating the first and second signals from the handpiece for delivery to the electrosurgical apparatus.

* * * * *